United States Patent [19]

Bussi et al.

[11] 4,085,054
[45] Apr. 18, 1978

[54] UTILIZATION OF ORTHOPHOSPHORIC ESTERS FOR THE PRODUCTION OF AQUEOUS FLUIDS FOR WORKING METALS

[76] Inventors: Giancarlo Bussi, Strada del Friuli, 85; Pierpaolo Baradel, Via Navali, 32, both of Trieste, Italy

[21] Appl. No.: 702,126

[22] Filed: Jul. 2, 1976

Related U.S. Application Data

[62] Division of Ser. No. 516,029, Oct. 18, 1974, Pat. No. 3,983,098.

[30] Foreign Application Priority Data

Oct. 18, 1973   Italy ..................................... 30279/73

[51] Int. Cl.² ............................................. C10M 3/04
[52] U.S. Cl. .................................. 252/49.3; 252/32.5; 260/963; 252/49.9
[58] Field of Search ................. 252/49.3, 32.5, 49.9; 260/963

[56] References Cited

U.S. PATENT DOCUMENTS 3,177,144  4/1965  Reamer et al. ...................... 252/49.3
3,496,104  2/1970  Shimada et al. ..................... 252/49.3
3,609,077  9/1971  Breitigam et al. .................. 252/32.5
3,945,931  3/1976  Bussi et al. .......................... 252/32.5

*Primary Examiner*—Benjamin R. Padgett
*Assistant Examiner*—Deborah L. Kyle
*Attorney, Agent, or Firm*—Haseltine, Lake & Waters

[57]   ABSTRACT

An aqueous composition for the working of metals comprising in solution in water at least one salt of an orthophosphoric ester of the formula:

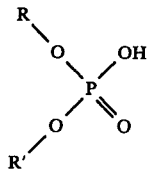

in which R is a hydrocarbon group containing between 10 and 20 carbon atoms and at least two atoms of chlorine, R' is hydrogen or a hydrocarbon group, identical or not to R, whose carbon chain contains between 10 and 20 carbon atoms and at least two atoms of chlorine.

10 Claims, No Drawings

UTILIZATION OF ORTHOPHOSPHORIC ESTERS FOR THE PRODUCTION OF AQUEOUS FLUIDS FOR WORKING METALS

CROSS-RELATED APPLICATION

This application is a Divisional Application of Ser. No. 516,029 filed Oct. 18, 1974, now U.S. Pat. No. 3,983,098 issued Sept. 28, 1976.

FIELD OF THE INVENTION

The present invention relates to products which are utilized in the working of metals in processes involving production of chips of material such as cutting and milling for example, or of deformation processes without production of chips such as rolling, stretching and drawing for example.

The invention relates, more particularly, to chemical compositions which, in aqueous solution, constitute bases for the formulation of liquids for the working of metals. These bases can generally be utilized alone or after having been mixed with relatively small quantities of additives, to serve one or a plurality of particular functions of aqueous fluids.

PRIOR ART

It is known that aqueous fluids utilized for the working of metals should have a number of properties among which can be mentioned: lubrication power, anti-corrosion power and the property of biodegradability; some other properties which can also be cited are the absence of formation of foam at the time of utilization, non-toxicity and absence of odor; finally, it is desirable that the products be inexpensive.

A number of fluids are already on the market which possess these properties in various degrees. However, many of these fluids are not aqueous solutions but are oil emulsions in water, and the characteristic principle of these fluids is that they are compositions of materials including a large number of very diverse materials each of which possesses a particular property which it is desired to confer to the fluid.

Many of these fluids, known in commerce under the name of "Synthetics for Mechanical Working" are aqueous solutions containing between 30 and 70% of a main constituent such as the condensates of alkylene oxides, soaps, corrosion inhibitors and foams, etc. These products are generally not biodegradable and, additionally, impose on the manufacturer complex operations to maintain their solubility and their particular properties. Additionally, they do not possess high pressure lubrication properties.

It is known that the phosphoric esters of fatty alcohols and phenols are good lubricants, their chemical formula being as follows:

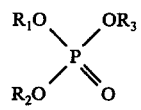

in which $R_1$, $R_2$ and $R_3$ are alkyl or aryl groups, identical or not, generally linear alkyl, and having between 7 and 20 carbon atoms.

SUMMARY OF THE INVENTION

The aim of the present invention is the realization of a novel base for aqueous fluids destined for the working of metal, said base being utilized in aqueous solution without additives and having, to a sufficient degree, the properties which have been mentioned above and particularly high lubrication power.

The invention, in consequent, has for an object alkali metal salts soluble in water and/or amine salts soluble in water, and/or ammonium salts soluble in water of orthophosphoric mono- and/or diesters of fatty alcohols and/or of fatty acid alcohols, the said esters being characterized in that the carbon chain of their molecule comprises chlorine atoms.

The chemical formulas of these mono- and diesters are the following:

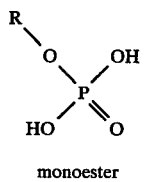 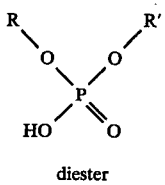

monoester          diester

R and R' are identical or not; they contain between 10 and 20 carbon atoms. As mentioned hereinabove, they also contain chlorine atoms which are attached to these groups.

Another object of the invention is constituted by the application of these chlorated orthophosphoric esters to the realization of aqueous fluids for the working of metals, the said application being characterized in that there is placed in water about 20 to 70% by weight of at least one alkaline salt and/or amine salt and/or ammonium salt of an orthophosphoric ester or of a mixture of orthophosphoric esters of the formula:

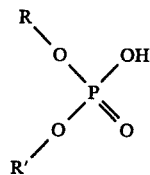

in which R is a group whose carbon chain has between 10 and 20 carbon atoms and contains at least two chlorine atoms and R' is hydrogen or a group identical or not to R whose chain contains between 10 and 20 carbon atoms and has at least two chlorine atoms.

Another object of the invention is the production of new bases for aqueous fluids adapted to the working of metals, of mixtures of:

at least one alkaline salt and/or amine salt and/or ammonium salt of a phosphoric ester described hereinabove, at least one alkaline salt and/or amine salt and/or ammonium salt soluble in water of the condensation products of a fatty acid and a carboxylic amino acid, hereafter designated as amido acid salts.

Applicants have described in their copending U.S. application of even date, now U.S. Pat. No. 3,945,931, issued Mar. 23, 1976, such amido acid salts as well as a process of synthesis of these salts. It is disclosed therein that among the condensation products cited hereinabove, amido acids having the general formula:

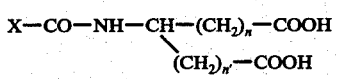

are particularly well suited. In this formula, X is a hydrocarbon group substituted or not by chlorine, containing between 9 and 25 carbon atoms, and $n$ and $n'$ are whole numbers or zero, identical or not, the sum of $n + n'$ being equal to 1 or 2.

The Applicants have noted in fact that the mixture of two types of products (salts of amido acids and salts of phosphoric esters) are particularly desirable for obtaining aqueous fluids for the working of metals. For this particular application, the production of these mixtures is made in the same manner as that of the salts of the phosphoric esters taken along and which will be described later; the two types can be mixed in all proportions, each of the two types possessing, individually, beneficial properties for this application as will be seen later for the orthophosphoric ester salts and as is explained in the aformentioned Applications for the amido acid salts. Thus, the two types can be mixed in proportions varying from 0 to 100% by weight.

A further object of the invention is a process of synthesis of the alkali metal salts and/or the amine salts and/or the ammonium salts of the chlorinated orthophosphoric esters, the said process being characterized in that it comprises the following main steps:

(1) esterification of phosphorus pentoxide and/or of orthophosphoric acid and/or phosphorus oxychloride by fatty alcohols and/or fatty acid alcohols containing between 10 and 20 carbon atoms and at least one double carbon to carbon bond;

(2) chlorination by addition, to the chains of the molecules of the obtained esters at the end of the first step; and (3) salification of the chlorinated esters obtained at the end of the second step by means of an alkaline base and/or an amine and/or ammonia.

The fatty alcohols utilized for the synthesis of the esters can have the general formula $R'' - CH_2OH$ in which $R''$ is a linear group, unsaturated and containing 9 to 19 carbon atoms; they can be substantially pure substances such as oleic acid for example in which $R''$ comprises 17 carbon atoms and a double bond in the 9 position or mixtures of alcohols of the general formula $R'' - CH_2OH$.

The alcohol can also have an acid function such as ricinoleic acid of the formula:

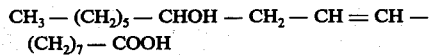

The first step of the process of the synthesis is the esterification of phosphorus pentoxide, $P_2O_5$ and/or orthophosphoric acid, $H_3PO_4$ and/or phosphorus oxychloride, $PO\ Cl_3$; the esterification should be effected in a perfectly anhydrous environment in an inert solvent. Thus, for example, there can be used suspension of phosphorus pentoxide in ether with the addition of the fatty alcohol or the fatty acid alcohol. The esterification is generally conducted at ambient temperature. Evaporation of the solvent after the reaction leads to the ester; this is generally a mixture of the mono- and the diester; if the operation is effected under the proper conditions, the triester is practically not formed. If the starting fatty alcohol has the formula $R'' - CH_2OH$, the obtained esters will have the following formulas:

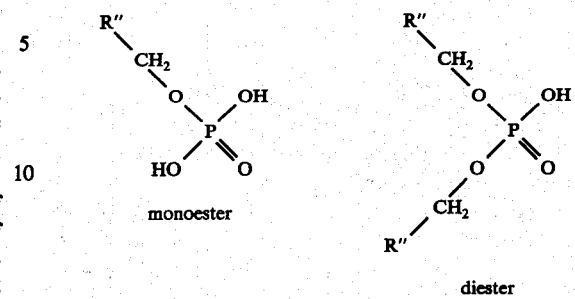

The second main step of the process is the chlorination by addition to the carbon chains of the molecules of the obtained esters. In this step, there is obtained the addition of one molecule of chlorine per double bond present in the ester molecules. The conditions of this reaction are known: the chlorine gas is bubbled in a solution of the esters in a solvent such as chloroform or hexane for example, at a temperature less than 0° C ($-10°$ C for example). After the reaction, the excess chlorine can be removed by passage of a gas such as nitrogen or air in the solvent, then by washing with water.

The esters contain as much chlorine as the number of ethylenic unsaturations contained in the molecule of the esters subjected to the chlorination.

The third main step of the process is the salification of the chlorinated ester molecules. This salification is effected by means of an alkali metal base such as sodium hydroxide, potassium hydroxide, or lithia or of an amine such as triethanolamine, morpholine, or ammonia in general; there is utilized a quantity of the base or of the amine in excess; this excess can, without disadvantage, be equal to more than two times the stoichiometric quantity.

The product thus obtained can be used in commerce alone or in admixture with the phosphoric ester salts as defined hereinabove, for a suitable use, in aqueous solution of 20–70%; the user can himself effect the final dilution to a working concentration generally between 2 and 10%.

Additionally, in order to perfect the characteristics of the employed product of the mixtures, it is possible to add additives thereto such as
anti-foam agents
bactericides
anti-corrosive agents
odor additives
colorants
agents to modify the physical characteristics.

The anti-foaming agents can be silicones, esters and special soaps.

Phenols, quaternary ammonium salts, nitrogen derivatives of alcohols, thiocarbonates, thiocarbamates, etc. which are known bactericides can be utilized herein.

The anti-corrosive agents can be alkaline nitrates, phosphates, borates, etc.

As odor control additives or colorants there can be used any of many conventional substances available on the market.

Finally, the agents for the modification of the physical properties of the product or the mixture can be alcohols, glycols, etc. which have been used conventionally as viscosity additives which are useful in aqueous solution or as is.

If oleyl alcohol is selected as the fatty alcohol and sodium hydroxide as the alkaline base, the salts of the orthophosphoric esters have the following chemical formula:

$$CH_3-(CH_2)_7-CHCl-CHCl-(CH_2)_7-CH_2-O\underset{Na}{\overset{O-Na}{\underset{O}{\overset{\diagdown}{P}\diagup}}}O$$

(monoester)

$$CH_3-(CH_2)_7-CHCl-CHCl-(CH_2)_7-CH_2-O\overset{O-Na}{\underset{O}{\overset{\diagdown}{P}\diagup}}$$
$$CH_3-(CH_2)_7-CHCl-CHCl-(CH_2)_7-CH_2-O$$

(diester)

The properties of these fluids can be determined by means of diverse methods. Applicant has determined the solubility in water by centrifugation of the aqueous solution and measuring the volume of the sediment; the anti-corrosive power by the IP 125 standard; the lubrication power by the standard of ASTM D 2783; the biodegradability by the relation of the biological oxygen demand of an aqueous solution (ASTM D 2329 – 68), during a determined time, to the chemical oxygen demand, which measures the necessary quantity of oxygen for complete oxidation for the same quantity of aqueous solution (ASTM D 1252 – 67).

The present invention is additionally illustrated by the following examples, which are given in the non-limiting fashion:

DESCRIPTION OF PREFERRED EMBODIMENTS

EXAMPLE I

In the following example, the fatty alcohol is oleyl alcohol;

(1) Preparation of the orthophosphoric esters

To 168 g of phosphorus pentoxide in suspension in absolute anhydrous ether, there are slowly added 804 g of oleyl alcohol; the atmosphere is maintained at a temperature of 25° C. After the reaction mixture has been agitated for 12 hours, it is filtered.

The ether is then evaporated. The obtained product weighs 900 g corresponding to a yield of 95% with respect to the oleyl alcohol quantity employed. The product is a mixture substantially of equimolecular parts of the orthophosphoric mono- and diesters.

(2) Chlorination of the ester mixture

In a bulb containing 481 g of the ester mixture obtained at the end of the first step, there is added 800 g of chloroform at a temperature of −10° C, and then chlorine gas is bubbled through the solvent. When the amount of chlorine in the effluent gas increases, the feed of chlorine to the bulb is terminated and there is effected three successive washings with 250 ml of water, and a subsequent drying on sodium sulfate.

The mixture is then filtered, and the solvent is evaporated, which leads to the obtention of 587 g of chlorinated products, corresponding to a proportion of 18% by weight of chlorine in the product; the yield of the chlorination is substantially quantitative.

(3) Salification of the mixture of chlorinated orthophosphoric esters

After measuring the index of acidity according to the method in ASTM D 974–64 (which leads to a value of 150 mg of potassium hydroxide per gram of mixture of chlorinated orthophosphoric esters), there is added to the mixture a quantity of morpholine 7.5 times greater than the stoichiometric quantity necessary for the obtention of the salts.

There is shown in the table situated at the end of Example II: the acidity index measured according to the method in ASTM D 974–64 of the chlorinated orthophosphoric ester mixture; the amount of chlorine and of phosphorus effected on the amine salt of the mixture of the pure chlorinated orthophosphoric esters; the solubility in water measured by the sedimented volume by centrifugation of an aqueous solution of the amine salt of the esters at 5%; the minimum concentration of the esters in distilled water satisfying the corrosion test according to IP 125 (i.e. obtention of the notation 0/0-0 according to this standard); the weld point measured according to ASTM D 2783 obtained for an aqueous solution of 1% of the amine salt of the esters which is a measure of the lubrication power, and; the biodegradability of an aqueous solution of the amine salt of the esters expressed by the relation $BOD_5/COD$ in which $BOD_5$ represents the quantity of oxygen consumed biologically in 5 days, and in which COD represents the quantity of oxygen necessary for a complete oxidation of the solution.

EXAMPLE II

In the following example, the fatty alcohol is an acid alcohol, namely ricinoleic acid. The process of synthesis is identical to that which has been described in Example I. There will be indicated hereafter the amounts or volumes of reactants only when they are different from those in Example I.

(1) Preparation of the orthophosphoric esters 886 g of commercial ricinoleic acid are reacted with 168 g of phosphorus pentoxide under the conditions of Example I.

975 g of product are obtained, corresponding to a yield of 95% with respect to the quantity of ricinoleic acid employed. The product is a mixture, substantially equimolecular, of the orthophosphoric mono- and diesters.

(2) Chlorination of the mixture of esters 519 g of the mixture of esters obtained at the end of the first step are dissolved in 800 g of chloroform under the conditions of Example I. There is obtained 600 g of the chlorinated product. The proportion of chlorine in the product is 18% by weight.

(3) Salification of the mixture of chlorinated orthophosphoric esters

After measuring the index of acidity according to the method in ASTM D 974-64 (which leads to a value of 194 mg of potassium hydroxide per gram of chlorinated phosphoric ester mixture) there is added to the mixture a quantity of morpholine equal to 7.5 times the stoichiometric quantity necessary for the obtention of the salts.

There is shown in the table hereafter the results of the contents and the measure of the properties of the mixture of the amine salts of the chlorinated orthophosphoric esters as well as, by way of comparison, the content and measures of the same properties of a commercial product ("Cimcool S.4. Cincinnati").

TABLE I

|  | EXAMPLE I | EXAMPLE II | Comparison Product (3) |
|---|---|---|---|
| Acidity index (before salification) mg KOH/g of ester mixture | 150 | 194 | 2.5 (determined on the product as is) |
| Chlorine content (before salification) % by weight | 18 | 18 | 2.5 (determined on the product as is) |
| Phosphorus content (before salification) % by weight | 5.4 | 3.5 | 0.32 (determined on the product as is) |
| Solubility in water of the amine salts; volume % sedimented | 0 | 0 | 0 (% sedimented in solution at 5%) |
| Corrosivity of the amine salts; minimum in % of non-corrosive esters of the solution at 1% - (1) | 0.5 | 1.7 | 2 |
| Lubrication power of the amine salts weld point in kg | 250 | 250 | 126 (solution at 5%) |
| Biodegradability $\frac{BOD_5}{COD} \times 100$ - (2) | 7 | 6 | 6 |

(1) There is mixed an excess of amine of 7.5 times the stoichiometric quantity necessary to obtain the salt.
(2) There is employed an excess of amine equal to 4 times the stoichiometric quantity necessary to obtain the salt.
(3) The product as is contains 45% of active material.

EXAMPLE III

This example is intended to illustrate the application to the realization of aqueous fluids for the working of metals of mixtures of amido acid salts and of phosphoric esters of fatty alcohols or acids (amido acid salts such as described in the copending application of even date, now U.S. Pat. No. 3,945,931, issued Mar. 23, 1976.

In the present example, the amido acid salt utilized is prepared from chlorinated tall oil, N-dichlorostearoylaspartic acid and triethanolamine.

The salt of the phosphoric ester is the salt of triethanolamine of dichlororicinolphosphoric acid.

There is obtained from these two salts two mixtures A and B in water, which contain (analyzed by functional criteria on the final obtained mixture):

|  | Mixture A (% in weight) | Mixture B (% in weight) |
|---|---|---|
| N-dichlorostearoylaspartic acid | 3.9 | 3.9 |
| Dichlororicinolphosphoric acid | 6.4 | 12.8 |
| Triethanolamine | 28.4 | 27.7 |
| Chlorinated tall oil | 11.3 | 5.6 |
| Water | 49.0 | 49.0 |
| Sodium Nitrite | 1.0 | 1.0 |

There is shown in Table II the results of the contents and the measure of certain properties of the mixtures obtained hereinabove, in comparison with the preceding control (Cimcool S.4 Cincinnati).

TABLE II

|  | Solution A | Solution B | Control |
|---|---|---|---|
| Amount of Chlorine (g/100 g of product) | 5.0 | 4.5 | 2.5 (determined on the product as is) |
| Amount of Nitrogen (g/100 g of product) | 2.80 | 2.77 | 0.32 (determined on the product as is) |
| Appearance of the aqueous solution | Limpid | Limpid | Limpid |
| Four-Ball Method standard ASTM D 2783 Weld Point in kg (solution at 5%) | 400 | 500 | 126 |
| Biodegradability = $\frac{BOD_5}{COD} \times 100$ | 14 | 12 | 6 |
| Corrosion test standard IP 125 Solutions at 4% | 0/0–0 | 0/0–0 | 0/0–0 |

Through the assembled results in the table, it is concluded that the mixtures of the salts of amido acids and of the salts of phosphoric esters constitute a good basis for the realization of aqueous fluids for the working of metals.

I claim:

1. An aqueous composition for the working of metals, said composition comprising in solution in water between 20 and 70% of at least one alkali metal, ammonium or amine salt of an orthophosphoric ester of the formula:

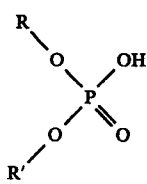

in which R selected from the group consisting of chlorinated hydrocarbon groups and chlorinated COOH-containing hydrocarbon groups, said chlorinated hydrocarbon groups having a $C_{10}$ to $C_{20}$ carbon chain and at least two atoms of chlorine, and R' is selected from the group consisting of hydrogen, chlorinated hydrocarbon groups and chlorinated COOH-containing hydrocarbon groups said chlorinated hydrocarbon groups having a $C_{10}$ to $C_{20}$ carbon chain and at least two atoms of chlorine and wherein R and R' may be the same or different.

2. A composition as claimed in claim 1 further containing an anti-foam agent.

3. A composition as claimed in claim 1 further containing bactericide.

4. A composition as claimed in claim 1 further containing an anti-corrosive agent.

5. A composition as claimed in claim 1 further containing an odor control additive.

6. A composition as claimed in claim 1 further containing a colorant.

7. A composition as claimed in claim 1 further containing a viscosity modifier.

8. A composition as claimed in claim 1 wherein the hydrocarbon group for R and R' is represented by the structure

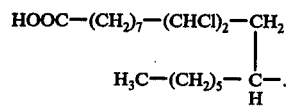

9. A composition as claimed in claim 1 wherein the hydrocarbon group for R and R' is represented by the structure

10. An aqueous composition for the working of metals, said composition comprising in solution in water between 2 and 10% of at least one alkali metal, ammonium or amine salt of an orthophosphoric ester of the formula:

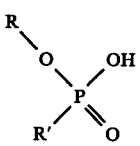

in which R is selected from the group consisting of chlorinated hydrocarbon groups and chlorinated COOH-containing hydrocarbon groups, said chlorinated hydrocarbon groups having a $C_{10}$ to $C_{20}$ carbon chain and at least two atoms of chlorine, and R' is selected from the group consisting of hydrogen, chlorinated hydrocarbon groups and chlorinated COOH-containing hydrocarbon groups said chlorinated hydrocarbon groups having a $C_{10}$ to $C_{20}$ carbon chain and at least two atoms of chlorine and wherein R and R' may be the same or different.

* * * * *